United States Patent [19]

Robbins et al.

[11] Patent Number: 5,726,061
[45] Date of Patent: Mar. 10, 1998

[54] METHOD OF DIAGNOSING AND MONITORING COLORECTAL CANCER

[75] Inventors: David Robbins; Robert B. Kirkpatrick, both of King of Prussia, Pa.; Stephen D. Holmes, Great Chishill, England

[73] Assignee: SmithKline Beecham Corporation, King of Prussia, Pa.

[21] Appl. No.: 727,210

[22] Filed: Oct. 8, 1996

[51] Int. Cl.⁶ ............ G01N 33/48; G01N 33/53; G01N 33/537; G01N 33/543
[52] U.S. Cl. .......... 436/64; 435/6; 435/7.1; 435/7.9; 435/7.91; 435/7.92; 435/7.93; 435/7.94; 435/7.95; 435/975; 436/578; 436/161; 436/162; 436/147; 436/173; 436/174; 436/165; 530/387.9; 530/387.1; 530/388.85; 530/389.1; 530/389.3

[58] Field of Search .............. 530/387.9, 387.1, 530/388.85, 389.3, 389.1, 388.25; 435/7.16, 7.9–7.95, 975; 436/578, 64, 161, 162, 147, 173, 174, 165

[56] References Cited

FOREIGN PATENT DOCUMENTS

WO 95/01995  1/1995  WIPO .
WO 95/02188  1/1995  WIPO .

*Primary Examiner*—Sheela Huff
*Attorney, Agent, or Firm*—William T. Han; William T. King; Edward T. Lentz

[57] ABSTRACT

Methods of screening for colorectal cancer by measuring levels of HC gp-39 are provided. Methods of monitoring patients with colorectal cancer are also provided. In addition, kits for detection of HC gp-39 useful in screening for and monitoring of colorectal cancer in a patient are provided.

4 Claims, No Drawings

METHOD OF DIAGNOSING AND MONITORING COLORECTAL CANCER

BACKGROUND OF THE INVENTION

Colorectal cancer is a leading cause of death in the western hemisphere. It is currently the second most common neoplasm, as well as the second leading cause of death due to cancer, in the United States. Risk factors for colorectal cancer include familial and genetic factors, and may include low levels of physical activity, alcohol consumption, high dietary intake of fat and meat and low intake of fiber and vegetables. Age also appears to be a significant risk factor as less than 2% of the cases occur in people under 40 years of age. The risk of colorectal cancer in a patient 50 years of age is 18 to 20 times that in a patient 30 years of age and the risk doubles about every 7 years thereafter.

The prognosis of colorectal cancer is directly related to the stage at which the cancer is detected. When detected early, either as an adenoma or wherein the tumor is confined to the bowel wall, the cancer can be treated effectively with a greater than 90%, five-year survival rate. However, in later stages, colorectal cancer spreads to local and regional lymph nodes, with the most common distant metastatic sites being the liver and the lung, thus making methods of treatment much less effective.

The World Health Organization in Geneva Switzerland has outlined certain requirements for determining when screening for a specific disease might be beneficial. First, the disease is a major cause of morbidity and/or mortality. Second, the treatment must be effective and risks of screening low. Third, the test must be both efficacious and cost-effective. Fourth, the test must have high sensitivity and specificity. Finally, the test must be acceptable to the general population and to the physicians who implement the screening. Colorectal cancer clearly meets these requirements. In fact, there are several tests currently being recommended by the American Cancer Society for colorectal screening, i.e., flexible sigmoidoscopy and fecal occult blood tests. Digital rectal examination has also been suggested. Wayne et al. *Arch. Fam. Med.*, 1995, 4, 357–366.

Flexible sigmoidoscopy, on average, currently costs more than $100 per procedure and has a complication rate of 4.5 per 10,000 persons screened. The 60-cm sigmoidoscope will reach approximately 55% of all colorectal cancer and is estimated to have an 85% sensitivity with a near 100% specificity. Eddy, D. M. *Ann. Intern. Med.* 1990, 113, 373–384. Sigmoidoscopy can be performed by primary care physicians and endoscopic nurses and is widely available. However, due to discomfort and embarrassment associated with this procedure, patient compliance with physicians' recommendations to undergo sigmoidoscopy is low, reportedly varying from 30 to 75%. Kelly, R. B. and Shank, C., *Med. Care*, 1992, 30, 1029–1042; McCarthy, B. D. and Moskowitz, M. A., *J. Gen. Intern. Med.* 1993, 8, 120–125.

Fecal occult blood testing (FOBT) costs much less. However, the sensitivity of the test is highly variably, ranging between 28% and 93%, depending upon the subject's hydration status, with a specificity of 96%. Eddy, D. M. *Ann. Intern. Med.* 1990, 113, 373–384. Allison et al. studied over 15,000 patients undergoing FOBT for up to 5 years. *Ann. Intern. Med.*, 1990, 112, 328–333. Their study concluded that evaluation of one of ten positive results of FOBT will reveal colorectal cancer and two of one thousand cancers will be missed because of false negative results. Additionally, if FOBT is the only method of screening used, Allison et al. estimate that approximately 50 to 60% of all colorectal cancers will be missed.

Accordingly, there is a need for additional cost effective, less invasive, screening methods for the early diagnosis and improved prognosis of colorectal cancer.

SUMMARY OF THE INVENTION

An object of the present invention is to provide a method of diagnosing colorectal cancer in a patient comprising screening for elevated levels of human cartilage glycoprotein, HC gp-39, in a sample from the patient. This method is also useful in monitoring patients who have been treated or are currently being treated for colorectal cancer.

Another object of the present invention is to provide a kit for diagnosing colorectal cancer which comprises antibodies against HC gp-39, a standard solution of HC gp-39 and a means for detecting HC gp-39.

These and other aspects of the present invention will become apparent to those skilled in the art from the teachings herein. It should be understood, however, that the following description and the specific examples, while indicating preferred embodiments of the invention, are given by way of illustration only. Various changes and modifications within the spirit and scope of the disclosed invention will become readily apparent to those skilled in the art from reading the following description and from reading the other parts of the present disclosure.

DETAILED DESCRIPTION OF THE INVENTION

The present invention is directed to the measurement of HC gp-39 levels and the use of such measurements in the diagnosis and monitoring of colorectal cancer. The measurement of HC gp-39 levels according to the invention is valuable in monitoring the effect of therapeutic treatment on a subject, detecting or diagnosing colorectal cancer and in predicting therapeutic outcome or disease prognosis.

The human cartilage glycoprotein, HC gp-39, is a protein with an apparent molecular weight of approximately 39 kDa secreted by explant cultures of both articular chondrocytes and synovial fibroblasts. Nyrikos and Golds *Biochem J.* 1990, 268, 265–268; Hakala et al. *J. Biol. Chem.* 1993, 268(34), 25803–25810. This protein has been described as a marker for joint injury, appearing in the blood and synovial fluid from patients diagnosed with rheumatoid arthritis. Johansen et al. *British J. of Rheumatology* 1993, 32, 949–955. The gene encoding this protein has been cloned and is expressed in tissues associated with rheumatic joints. Hakala et al. *J. Biol. Chem.* 1993, 268(34), 25803–25810. The protein YKL-40 has also been identified as one of the major secretory products of cultured human osteoblastic cells (osteocarcinoma cell line MG-63) expressed in response to 1,25-dihydroxyvitamin D3 stimulation. Johansen et al. *J. Bone and Min. Res.* 1992, 7(5), 501–511; Johansen et al. Br. J. Rheumatol. 1993, 32, 949–55. The N-terminal portion of YKL-40 was sequenced and found to be identical to HC gp-39. Upon further sequencing, YKL-40 and HC gp-39 were found to be identical.

A number of experiments have been performed which point to the role of HC gp-39 as a product of macrophages. Primary human monocytes, activated to become macrophages through adherence to plastic, secrete high levels of HC gp-39 into the culture media. In addition, the induction of HC gp-39 expression has been correlated with the differentiation of myeloid cell lines HL60 and U937 toward a macrophage lineage by induction with phorbol ester. HC gp-39 message can be detected in human atherosclerotic plaques derived from enarterectomies. Accordingly, it is believed that the HC gp-39 protein functions in various tissues undergoing extensive remodeling, such as, for example, myeloid and macrophage cells, including those cells associated with rheumatoid arthritis and atherosclerosis where macrophages play an important role. Further, rHC gp-39 was shown to stimulate in vitro smooth muscle migration, indicative of involvement in the remodeling processes occurring in diseased arteries.

It has now been found that detection of elevated levels of human cartilage glycoprotein, HC gp-39 serves as screening method for early detection of colorectal cancer in patients. By "elevated levels" it is meant an amount of HC gp-39 in a patient sample that is at least 2-fold higher than an amount of HC gp-39 measured in control samples, i.e., blood from normal patients not having colorectal cancer. Measuring the levels of this protein in a patient can also be used to monitor the disease status of the colorectal cancer in patients who have undergone treatment for colorectal cancer or who are currently undergoing treatment for colorectal cancer. In this method, decreasing or stable levels of HC gp-39 in a patient, as compared to a baseline level previously determined in the same patient, are indicative of the treatment being effective against the colorectal cancer. As used herein, a "sample" refers to a collection of cells and the biological fluid in which they were obtained. HC gp-39 protein may be measured in samples of whole blood, plasma, or serum, for example.

Thus, in one embodiment, the present invention relates to a method for detecting altered levels of HC gp-39 protein in a patient sample. Assays used to detect levels of these proteins are well-known to those of skill in the art and include radioimmunoassays, competitive-binding assays, Western Blot analysis, ELISA and sandwich immunoassays.

For example, an automated immunoassay for detection of HC gp-39 in serum or plasma samples has been developed. In this assay, microtiter well plates are coated with monoclonal antibody against HC gp-39, mAb 11H4 (2 µg/ml, 100 µl/well, in phosphate buffered saline, pH 7.4), overnight at 4° C. Following the incubation, the solution is aspirated and any available binding sites left on the plate are blocked with 1% bovine serum albumin (BSA) in Tris buffered saline, pH 7.4 (250 µl/well. The wells are then washed four times to remove excess blocking solution. A 50 microliter aliquot containing 2 µg/ml biotinylated mAb 17D12 is then added to each plate in Eu assay buffers (Wallac, Turku, Finland) plus 2% mouse serum followed by a 50 microliter aliquot of plasma or serum to be tested. The plates are incubated for 60 minutes on a shaker at room temperature. The wells are then washed four times. Streptavidin-Eu (Wallac), 100 µl/well in Eu assay buffer, is added and the plates are incubated again for 30 minutes on a shaker at room temperature. Following the incubation, the wells are washed four times again; one hundred microliters of enhancer is added to each well; and after a five minute incubation, the fluorescence is measured. The sensitivity of the assay is approximately 100 pg/ml and is linear up to concentrations of 100 ng/ml. Plasma and serum samples measured with the assay when diluted out in the range of ½ to 1/32 have a mean recovery of 102+/−5%. Recovery of spiked HC gp-39 into serum or plasma is 98+/−2%.

Using this immunoassay, HC gp-39 levels in patients with varying states of colorectal cancer were determined. Results from this assay are shown in the following Table 1.

TABLE 1

HC gp-39 Correlation with Disease Status

| Disease Status | Number of Patients | Mean HC gp-39 (ng/ml) | Std. Dev. | Low Range | High Range |
|---|---|---|---|---|---|
| Normal | 18 | 19.4 | 8.3 | 6.2 | 45.8 |
| Progressive | 16 | 148.4 | 45.0 | 42.0 | 241.2 |
| Responding | 7 | 137.5 | 49.4 | 70.2 | 264.6 |
| Stable | 13 | 99.1 | 49.1 | 20 | 259.6 |

Accordingly, serum from patients suffering from progressive colorectal cancer contained on average 7.6 fold higher levels of HC gp-39 than serum from normal controls. Serum from patients with colorectal cancer responsive to treatment contained, on average, 7.1 fold higher levels of HC gp-39, while serum from stable patients who suffered from colorectal cancer previously but showed no signs of the cancer for at least 5 years contained, on average, 5.1 fold higher levels of HC gp-39 than serum from normal controls.

As will be obvious to those of skill in the art upon this disclosure, other means for determining HC gp-39 levels can also be used. For example, a competition assay may be employed wherein antibodies specific to the HC gp-39 protein are attached to a solid support and labeled protein and a sample derived from the patient are passed over the solid support and the amount of label detected attached to the solid support can be correlated to a quantity of HC gp-39 protein in the sample.

The present invention also provides kits for diagnosing colorectal cancer and monitoring the status of the disease by determining HC gp-39 protein levels in a biological sample. Such kits comprise a first antibody against HC gp-39, preferably a monoclonal antibody such as mAb 11H4 or mAb 17D12. However, other monoclonal antibodies against HC gp-39 can also be prepared using any technique which provides antibodies produced by a continuous cell line culture. Examples of such techniques include the hybridoma technique (Kohler and Milstein *Nature* 1975, 256, 495–497), the trioma technique, the human B-cell hybridoma technique (Kozbor et al. *Immunology Today* 1983, 4, 72), and the EBV-hybridoma technique to produce human monoclonal antibodies (Cole et al. in *Monoclonal Antibodies and Cancer Therapy*, Alan R. Liss, Inc., 1985, pages 77–96). Kits of the present invention will further comprise a HC gp-39 standard and a means for detecting HC gp-39. Means for detecting a protein are well known in the art. For example, in one embodiment, the kit may further comprise a second antibody against HC gp-39 which is biotinylated. The biotinylated antibody, when bound and immobilized to HC gp-39 can be detected with streptavidin. Alternatively, the first or a second antibody against HC gp-39 can be delectably labeled with a radioisotope, fluorophore or enzyme. The kits of the present invention may further comprise a solid support capable of binding either a first antibody against HC gp-39 or HC gp-39. Examples of solid supports include, but are not limited to, microtiter well plates, slides and beads.

The following examples are provided for illustrative purposes only and are not intended to limit the invention.

EXAMPLES

Example 1

Expression of HC gp-39 in vitro

Recombinant HC gp-39 was produced in vitro by transfecting an expression vector containing the cDNA into CHO cells and selecting stable cell lines.

The full length HC gp-39 gene was cloned into CDN in two pieces; a 660 bp Sac II-Bst EII fragment plus a 678 bp Bst EII-Bcl fragment, ligated together with the CDN vector cut with Sac II-Bcl I. This construct was transfected into CHO ATCC 317 cells by standard methods. Specifically, 20 mg of the HC gp-39 plasmid construct was linearized by restriction digestion and electroporated into $1.25\times10^7$ cell in 1 ml. Cells were seeded at a density of $2.5\times10^3$ cells per well and selected in minimal media in the absence of nucleosides. Secreted protein was recovered from the conditioned media and purified using Q Sepharose flow through, S Sepharose capture and sized on Suprose 12. The resulting material was greater than 95% pure as determined by Coomassie blue staining.

Example 2

Production and characterization of antibodies generated against HC gp-39

Murine monoclonal antibodies were produced using purified rHC gp-39. Purified rHC gp-39 was used as the immunogen for a panel of four female mice (CB6/FI). The animals received one subcutaneous injections of rHC gp-39 in phosphate buffered saline (PBS) emulsified with a one to one ratio of Freund's complete adjuvant and booster injections in Freund's incomplete adjuvant i.p. The priming antigen dose and boosts were 20 µg. After boosts, serum samples were collected and assayed for binding to rHC gp-39. Animals producing serum samples that bound rHC gp-39 were selected as spleen donors and boosted i.p. with 63 µg rHC gp-39 prior to euthanasia.

The fusion procedure, first reported by Kohler et al. (*Nature* 1975, 256, 495) was used with modifications (Zola, H. "Monoclonal antibodies: a manual of techniques", CRC Press, Boca Raton, Fla., 1987). Spleen cells from a donor mouse were pooled and fusions performed using a ratio of five spleen cells to one X63.Ag8.653 myeloma cells. Supernatants from fusion-positive wells were assayed by binding to rHC gp-39 by immunoassay.

Monoclonal antibodies (2G10, 5C11, 11C4, 17D12, 18B3, 11H4, and 5C12) were characterized for their ability to immunoprecipitate HC gp-39 with protein A Sepharose. In addition, these monoclonal antibodies have been tested for their ability to neutralize binding of HC gp-39 to sites found in lung tissue. Several of these mAbs both immunoprecipitate and neutralize binding activity (mAbs 2G10, 5C12, 18B3, 11H4, 11C4, 17D12, 5C11) over a range (from 0.01 mg/ml to 1 mg/ml).

Example 3

Biotinylation of mAb 17D12

To a microfuge tube was added: 131 µl (0.2 mg of 1.52 mg/ml stock solution) of mAb 17D12; 396 µl 0.1M carbonate/bicarbonate buffer, pH 9.6; and 12 µl biotin reagent (Amersham Corp, Cat. # RPN 2022, Arlington Hts., Ill.). The microfuge tube was then incubated for 60 minutes at room temperature with rotation, followed by pulse centrifugation The biotinylated Mab 17D12 was separated from free biotin using a NAD-5 column (Pharmacia, Piscataway, N.J.) according to the manufacturer's instructions.

What is claimed is:

1. A method of screening for colorectal cancer in a patient comprising:

(a) obtaining a sample from a patient;

(b) measuring levels of HC gp-39 (human cartilage glycoprotein-39) in the patient sample; and (c) comparing the measured levels of HC gp-39 in the patient with levels measured in control samples to determine whether levels of HC gp-39 are elevated in the patient wherein said control samples are samples from normal patients not having colorectal cancer.

2. The method of claim 1, wherein the patient and control samples comprise whole blood, plasma or serum.

3. A method of monitoring colorectal cancer in a patient currently undergoing treatment or having undergone treatment for colorectal cancer comprising:

(a) determining a baseline level of HC gp-39 (human cartilage glycoprotein-39) in a sample from a patient;

(b) measuring levels of HC gp-39 in subsequently obtained samples from the same patient; and (c) comparing the measured levels of HC gp-39 with the baseline level of HC gp-39 in the patient.

4. The method of claim 3 wherein the samples comprise whole blood, plasma or serum.

* * * * *